(12) United States Patent
Prince

(10) Patent No.: US 10,765,814 B2
(45) Date of Patent: Sep. 8, 2020

(54) SAFETY SYRINGE ASSEMBLY

(71) Applicant: Ty L. Prince, Knoxville, TN (US)

(72) Inventor: Ty L. Prince, Knoxville, TN (US)

( * ) Notice: Subject to any disclaimer, the term of this patent is extended or adjusted under 35 U.S.C. 154(b) by 0 days.

(21) Appl. No.: 16/560,044

(22) Filed: Sep. 4, 2019

(65) Prior Publication Data

US 2020/0069885 A1 Mar. 5, 2020

Related U.S. Application Data

(63) Continuation-in-part of application No. 62/727,136, filed on Sep. 5, 2018.

(51) Int. Cl.
*A61M 5/32* (2006.01)

(52) U.S. Cl.
CPC ........ *A61M 5/3202* (2013.01); *A61M 5/3219* (2013.01); *A61M 5/3245* (2013.01); *A61M 2005/3217* (2013.01); *A61M 2005/3246* (2013.01); *A61M 2005/3247* (2013.01); *A61M 2005/3253* (2013.01)

(58) Field of Classification Search
CPC .............. A61M 5/3202; A61M 5/3219; A61M 5/3245; A61M 2005/3217; A61M 2005/2496; A61M 2005/3125; A61M 2005/3246; A61M 2005/3247; A61M 2005/3253
See application file for complete search history.

(56) References Cited

U.S. PATENT DOCUMENTS

| 4,436,479 | A | 3/1984 | Belloli | |
|---|---|---|---|---|
| 6,322,540 | B1 | 11/2001 | Grabis | |
| 7,513,887 | B2 * | 4/2009 | Halseth | A61M 5/3232 604/110 |
| 9,078,978 | B2 | 7/2015 | Schraga | |
| 9,554,736 | B2 | 1/2017 | Gupta et al. | |
| 2005/0101918 | A1 | 5/2005 | Chen et al. | |
| 2015/0065960 | A1 * | 3/2015 | Osman | A61M 5/3129 604/189 |
| 2017/0106149 | A1 | 4/2017 | Clawson | |
| 2017/0156983 | A1 | 6/2017 | Tennican | |

* cited by examiner

*Primary Examiner* — Laura A Bouchelle
*Assistant Examiner* — Justin L Zamory
(74) *Attorney, Agent, or Firm* — Gerald R. Black, Esq.

(57) ABSTRACT

The safety syringe assembly is for inserting a needle into a patient and comprises a needle hub assembly and a safety cover. The needle hub assembly includes a needle, needle hub, and hub flex unit. The needle is mounted on the front side of the needle hub while the rear side is for receiving a syringe. The safety cover houses the needle hub assembly in a first position during shipping, a second position during insertion of the needle into the patient, and in a third position after the needle has been inserted into the patient while awaiting disposal. A portion of the safety cover includes magnification enabling a user to view a dosage calibration scale, needle bevel and air bubbles. The hub flex unit assumes a first enlarged position during shipping, is compressed during insertion into the patient, and slides into a third position after usage while awaiting disposal.

20 Claims, 13 Drawing Sheets

Safety Cover with Breakaway Cap

Needle Hub Assembly - Front

Needle Hub Assembly - Rear

Needle Flex Unit

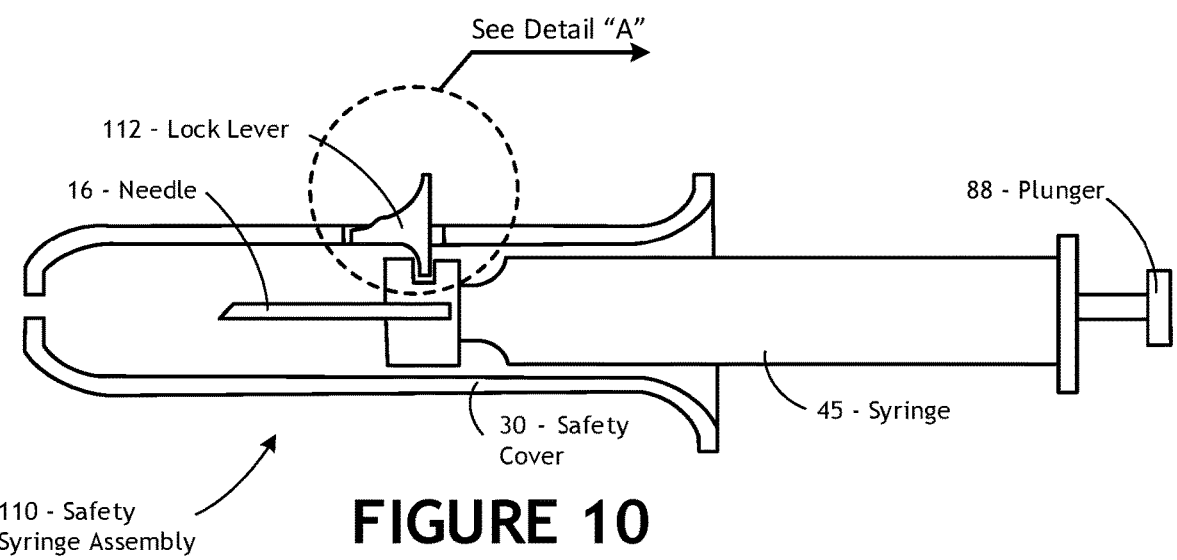
FIGURE 10
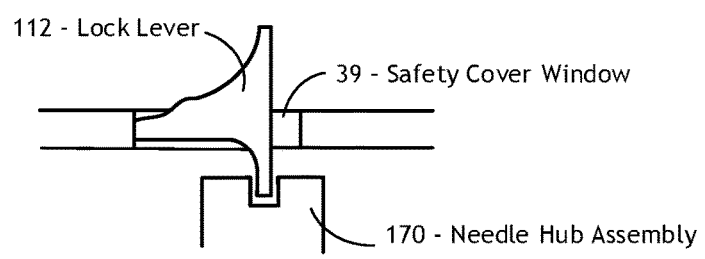
Detail "A"

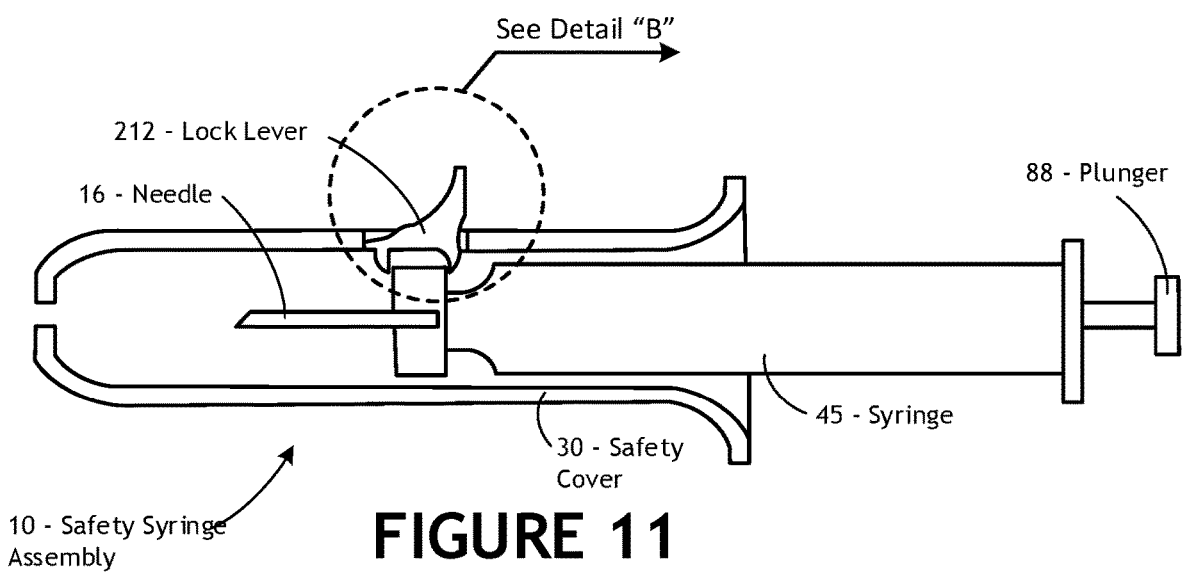
FIGURE 11
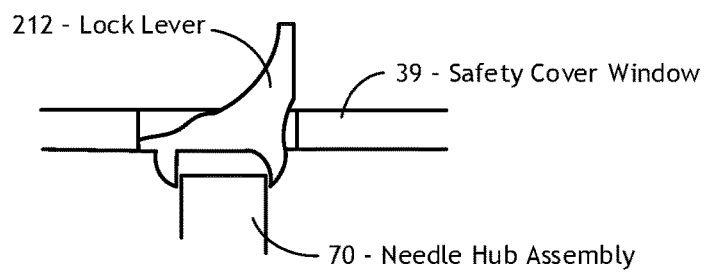
Detail "B"

Needle Hub Assembly - Front

Needle Hub Assembly - Rear

SAFETY SYRINGE ASSEMBLY

CROSS-REFERENCE TO RELATED APPLICATIONS

This application is related to and claims priority to U.S. Provisional Application No. 62/727,136, entitled "Safety Syringe Assembly" (Ty L. Prince), filed on Sep. 5, 2018.

FIELD OF THE INVENTION

This invention relates generally to medical protective devices and more particularly, to an improved shielding apparatus for use with syringes to achieve needle protection, one handed operation, a product to improve injection efficiency and comfort and consistent bevel orientation.

BACKGROUND OF THE INVENTION

Many medical conditions require treatment that includes medication administered through injections. Injections may be administered on a regular schedule, and patients needing regular injections often inject the medication themselves. Also, accidental stabs from handling syringes and needles are a common problem and can result in transmission of serious diseases.

In addition, conventional syringes may cause problems in inserting a needle at the correct location and minimizing the amount of pain caused.

Beveled needle tips are often used to ease the pain associated with inserting the needle into the skin. The sharp pointed bevel enables a user to accurately target an injection site.

Efforts to properly orientate the bevel of the needle have been made for several decades. Some representative efforts include:

U.S. Patent Document No. 20170156983 (Tennican) discloses a syringe device for mixing and administering a medicant. The system includes a medicant vial; a syringe assembly comprising a barrel and a piston; a protective material supporting the syringe assembly and medicant vial; and a member within the system, the member separating the piston of the syringe assembly from the medicant vial. Systems are provided that can include a syringe assembly comprising a barrel and a piston having a forward end and an opposing back end, a protective material supporting the syringe assembly, and a needle housing coupled to the protective material.

U.S. Pat. No. 9,554,736 (Gupta; et al.) discloses a device with integrated allergy testing which provides an allergy detection system for use during catheterization. The allergy detection system is incorporated into specialized syringes, connectors for use with standard syringes, or can be an independent test module designed for the sole purpose of allergy detection. The detection system features a test strip, and a structure to couple the system to a connector, syringe or a housing, to form an independent test module. The detection system is used to detect potential allergic reactions.

U.S. Pat. No. 4,436,479 (Belloli) discloses a device is described for orienting intravenous needles or other similar articles having relatively long shank portions which terminates in beveled or flat tips. The device has a fixture for supporting the needles at an angle to the horizontal and with the beveled tip resting on a knife edge. A vibrator is coupled to the needle supporting fixture causing the needle to turn to its most stable position on the knife edge where the flat portion engages the knife edge.

There is a need for a safety syringe system that shields needles and protects a user after an injection is administered without requiring a user to carefully replace a small cap on the needle. There is also a need for syringe systems that facilitates orientation of the needle bevel to give accurate injections and reduce patient pain. Proper intradermal allergy testing requires that the needle bevel should always be inserted bevel up and then rotated bevel down, so that a precise amount is injected into the area every time (This prevents false positives and false negative results because a positive test is defined as an increase in size of 3.0 mm or greater compared to a saline wheal). In addition, injecting with the bevel down prevents backsplash, which occurs when someone injects bevel up and does not insert the needle bevel all the way under the skin.

Although the art has provided improved devices to facilitate the removal and re-engagement of needle guards while lowering the possibility of accidental needle pokes there is still a need for a simple, straight-forward, reliable, easily fabricated device for the removal and replacement of a needle cover which holds the needle cover in a releasable secure position.

An object of the present invention is to minimize the possibility of a misuse of the needle cover and thereby the possibility of an accidental needle poke.

Still, another object of the present invention is to provide a user-protective syringe holder that is compatible with syringes of different manufacturers, and which vary somewhat in size.

Accordingly, an object of the present invention is to provide an improved means for orienting intravenous needles, allergy needles or similar articles having elongated shanks with beveled tips.

SUMMARY OF THE INVENTION

The safety syringe assembly of the present invention addresses these needs and these objectives.

The safety syringe assembly is for inserting a needle into a patient.

The safety syringe assembly comprises a needle hub assembly and a safety cover. The needle hub assembly includes a needle, a needle hub, and a hub flex unit. The needle is mounted on the front side of the needle hub. A syringe is attachable to the rear side of the needle hub.

The hub flex unit is mounted upon the needle hub and includes a flex arm and a flat. The flex arm prevents the needle hub assembly from sliding during shipping and the flat prevents the needle hub assembly from rotating within in the syringe cover during shipping.

The safety cover secures the needle hub assembly in a first position during shipping. The safety cover secures the needle hub assembly in a second position during insertion of the needle into the patient. The safety cover secures the needle hub assembly in a third position after the needle has been inserted into the patient while awaiting disposal. A portion of the safety cover includes magnification enabling a user to view a dosage calibration scale, the needle bevel and air bubbles.

The hub flex unit assumes a first enlarged position during shipping, is compressed during insertion into the patient, and slides back into a third position after usage while awaiting disposal.

Still other objectives of the safety syringe assembly of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIG. 10 depicts still another preferred embodiment of the safety cover for use with the safety syringe assembly of the present invention with a lock lever to enable unobstructed movement of the needle hub assembly from the second position to the third position along with a Detail "A" of the lock lever.

FIG. 11 depicts yet still another preferred embodiment of the safety cover for use with the safety syringe assembly of the present invention with a lock lever to enable unobstructed movement of the needle hub assembly from the second position to the third position along with a Detail "B" of the lock lever.

FIG. 12A depicts a front side view and FIG. 12B depicts a rear detail view of a second preferred embodiment of the safety cover and needle hub assembly of FIGS. 1A, 1B, and 1C, including the needle, a needle hub, and a needle flex unit. Also depicted is the needle hub indexing flat toward the magnifier. This design insures that the needle is always pointed upward toward the red stripe, is always 90 degrees from the needle hub flat and that the needle, the needle bevel, the needle hub are always indexed, with respect to the safety cover, enabling the needle bevel to be toward the red stripe, when viewed through the magnifier or gives the user knowledge of the position of the needle bevel position relative on the safety cover.

DETAILED DESCRIPTION OF THE PRESENT INVENTION

Figure 1A:
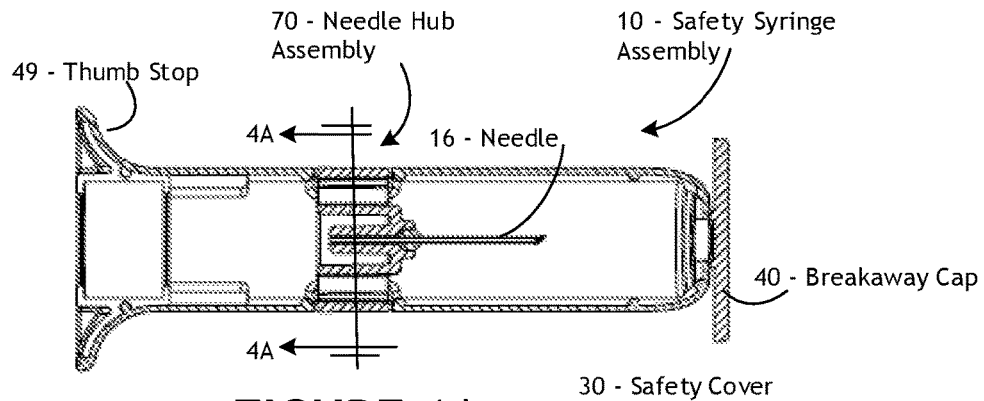
FIG. 1A depicts a side elevational view of a first preferred embodiment of a safety syringe assembly of the present invention, with a needle hub assembly in a first position for shipping.
Figure 1B:
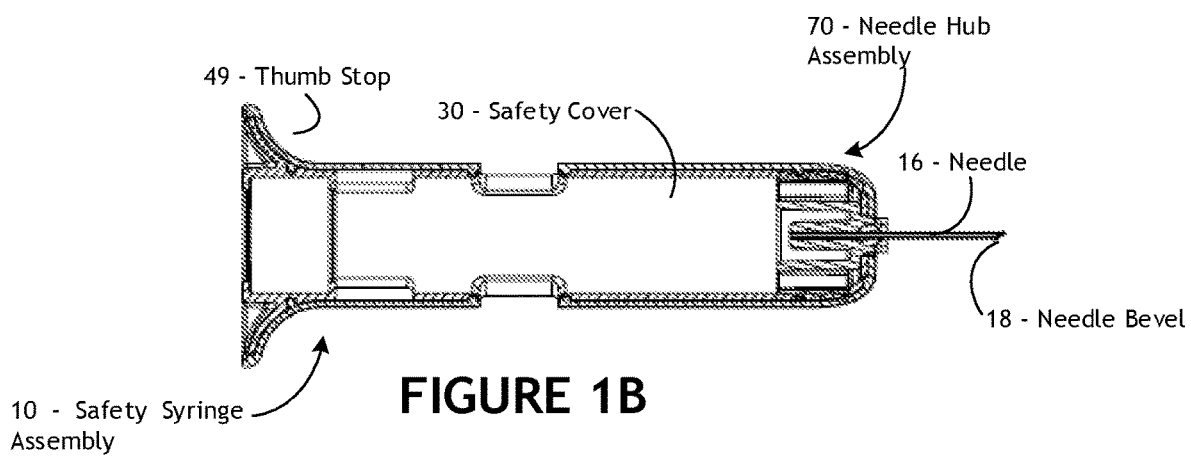
FIG. 1B depicts a side elevational view of the safety syringe assembly of FIG. 1A, with a needle hub assembly in a second position for insertion of the needle into the skin of the patient.
Figure 1C:
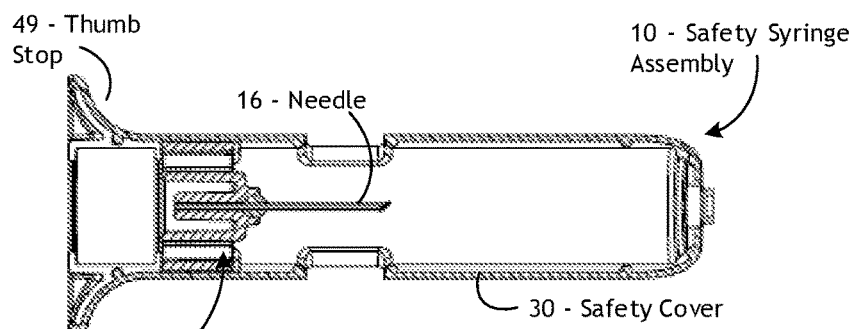
FIG. 1C depicts a side elevational view of the safety syringe assembly of FIG. 1A, with a needle hub assembly in a third position, the safety syringe assembly having been used and awaiting disposal.

Referring now to the drawings, FIGS. 1A, 1A, and 1C each depict side elevational views of a first preferred embodiment of a safety syringe assembly of the present invention [10].

The safety syringe assembly of the present invention [10] preferably comprises a needle hub assembly [70] and a safety cover [30].

FIG. 1A depicts the safety cover [30] housing the needle hub assembly [70] in a first position for shipping. FIG. 1B depicts the safety cover [30] housing the needle hub assembly [70] in a second position for insertion of the needle [16] into the skin of the patient. FIG. 1C depicts the safety cover [30] housing the needle hub assembly [70] in a third position, the safety syringe assembly [10] having been used and awaiting disposal.

The needle hub assembly [70] includes a hub flex unit mounted upon a needle hub [76], and the needle hub [76] for retaining the needle [16] securely mounted therewithin. The hub flex unit includes a flex arm [77] and a flat [78]. The flex arm [77] prevents the needle hub assembly [70] from sliding within the safety cover [30] during shipping. The flat [78] prevents the needle hub assembly [70] from rotating within the safety cover [30] during shipping.

The needle hub assembly [70] is preferably color coded at the factory, for either a long injection needle (for example, blue) or a shorter needle for testing (for example, white).

This ensures that the proper needle length is used for either injection or testing. The current needles used in the industry color code the cap. The cap is a separate piece which can be switched. If the color-coded caps are switched, a longer injection needle may be used for testing and a shorter testing needle may be used for injections. Using the incorrect needle length can give false allergy test results or not enable the allergy fluid to be injected to the proper depth under the skin.

In addition, the safety cover [30] preferably uses visual indicators or alignment markers [33 and 34], such as colored stripes (for example, a green and a red stripe on the safety cover [30]) to indicate the orientation of the needle bevel [18]. In this example, red shows bevel [18] up for insertion under the skin and the green shows the needle bevel [18] down for dispensing of the fluid under the skin.

The safety cover [30] is made of clear material enabling light to enter the safety cover [30] providing for a clear view of the needle bevel [18] orientation, the needle length, as well as enabling light into the safety cover [30] for the reading of the syringe volume scale [46], through the lens, during the process of filling the syringe [45] from the vial of allergy fluid.

The safety cover [30] preferably protects either a short needle [16] for testing or a longer needle [16] for injections. The safety cover [30] includes a window [39].

The safety syringe assembly of the present invention [10] enables one-handed operation by the medical technician or user.

The safety cover [30] and needle hub assembly [70] of the present invention are both indexed to the needle bevel [18] ensuring that during either testing or injection, the needle bevel [18] is up for insertion and down for dispensing. The current needle used in the allergy industry is not indexed to the needle bevel [18]. This enables the needle bevel [18] to be inserted in any orientation and dispensed in any orientation. This current product is deficient in that it does not enable the proper circular bubble to be created under the skin for testing (enabling false positives or no positive at all) and can cause the fluid to be sprayed back onto the medical technician or user during injection.

The safety cover [30] has now moved past the original position with the needle hub pads locked into recesses into this safe (disposal) pocket of the safety cover [30]. Once in this position, the needle [16], needle hub [76], safety cover [30] and syringe [45] can be disposed of together or the needle [16], needle hub [76] and safety cover [30] can be removed from the syringe [45] and disposed of separately.

Figure 2:
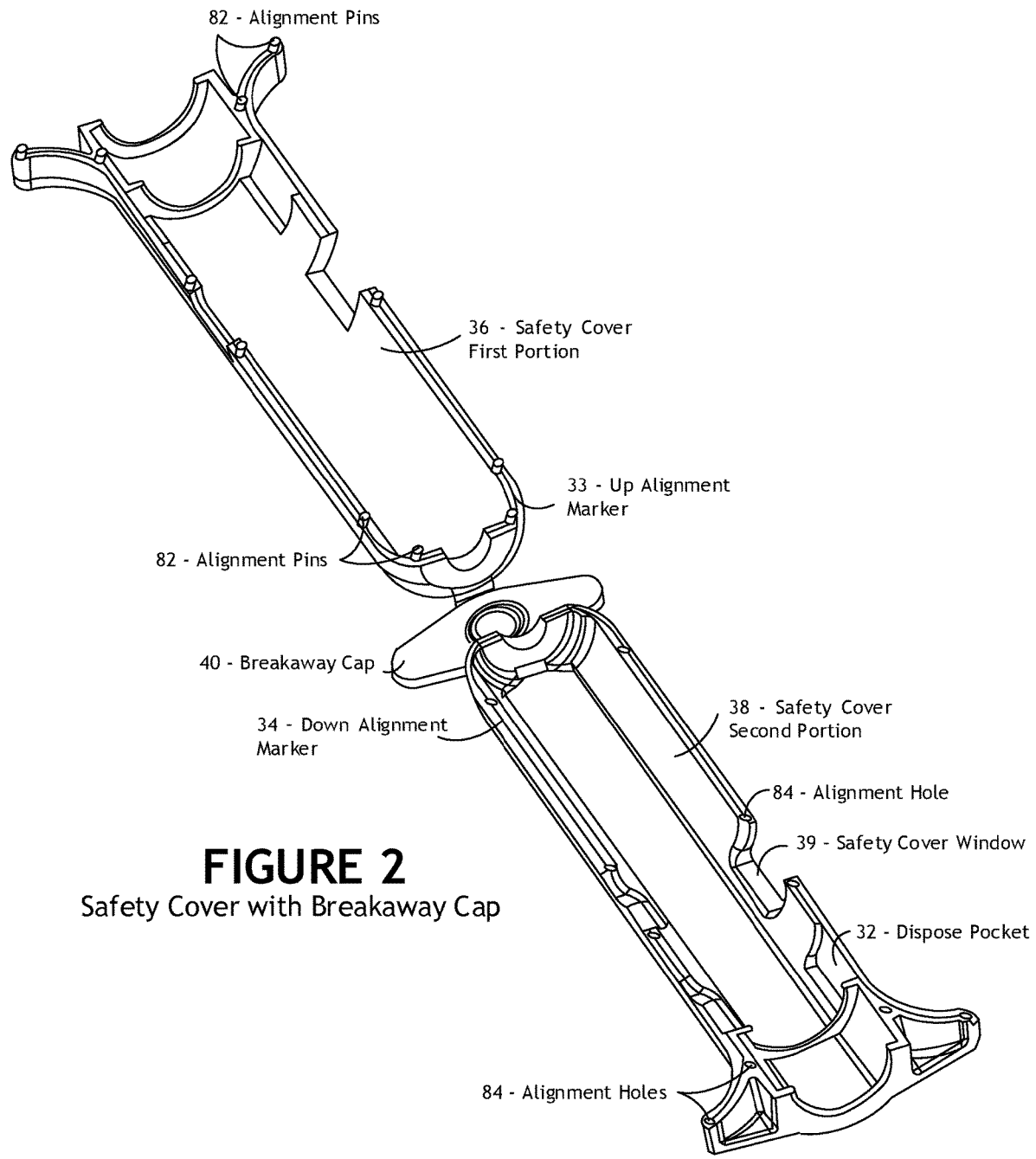
FIG. 2 depicts a side elevational view of the safety cover for use in the safety syringe assembly of FIGS. 1A, 1B, and 1C, the safety cover including two halves joined together by a safety cover.

FIG. 2 depicts a side elevational view of the safety cover [30] for use in the safety syringe assembly [10] of FIGS. 1A, 1B, and 1C, the safety cover [30] including two halves joined together by a breakaway cap [40]. The breakaway cap [40] is attached to both halves of the safety cover [30], holding them together and in position, relative to each other, until needle hub assembly [70] can be placed into the safety cover [30] and the breakaway cap [40] glued closed. Preferably, the two halves of the safety cover [30] are glued together. The adhesive is applied as recommended by the manufacturer taking care to avoid the hub assembly and the windows [39].

Also depicted are the two openings for the needle hub pads assemblies, an initial position, as well as the locking recesses used to lock the needle hub assembly [70] into a disposal position.

The assembly is closed, clamped and cured per manufacturer instructions. Packaging and sterilization protocols are then followed.

Figure 3A:
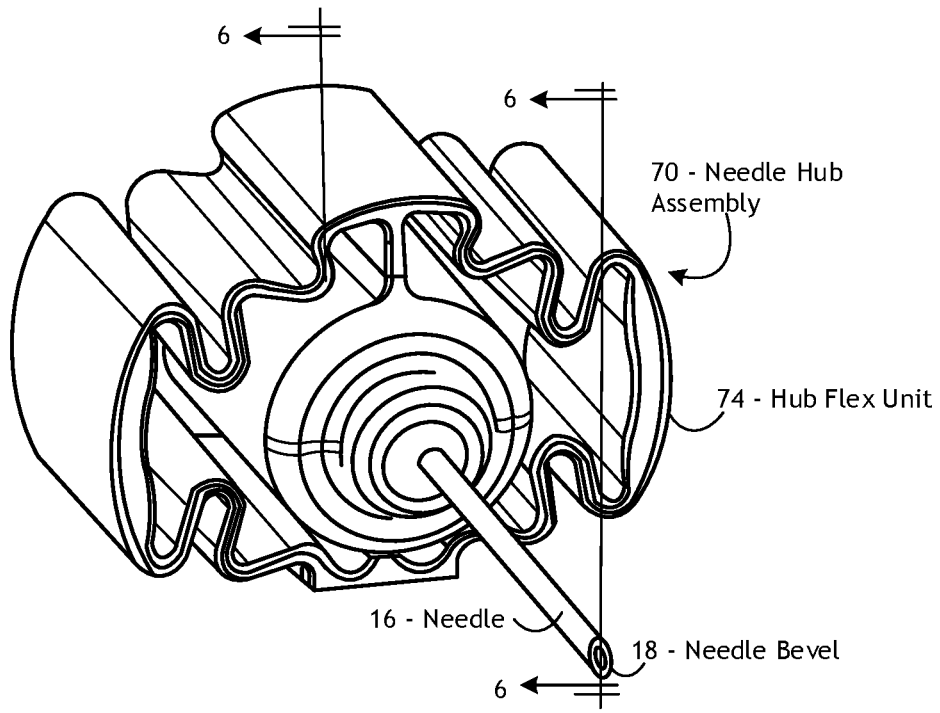
FIG. 3A depicts a front view and FIG. 3B depicts a rear view of a first preferred embodiment of the needle hub assembly of FIGS. 1A, 1B, and 1C, including the needle, a needle hub, and a needle flex unit.
Figure 3B:
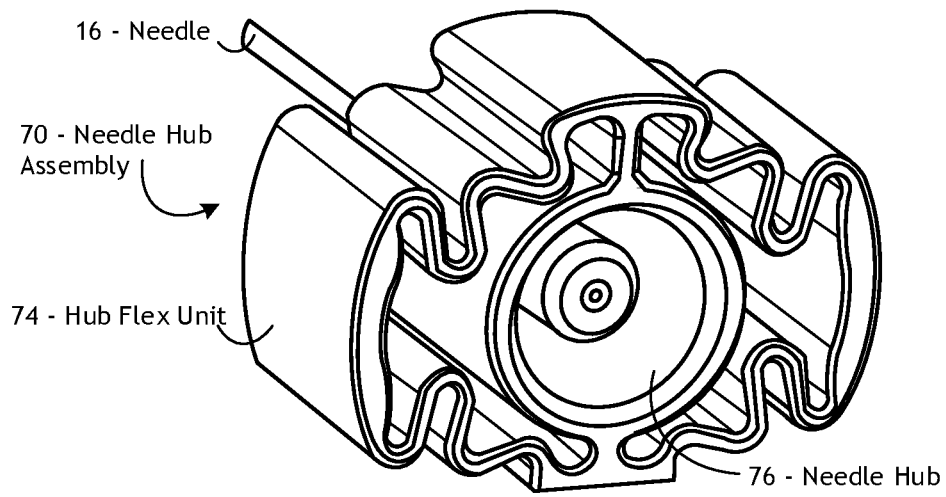

FIG. 3A depicts a front view and FIG. 3B depicts a rear view of a first preferred embodiment of the needle hub assembly [70] of FIGS. 1A, 1B, and 1C, including the needle [16], a needle hub [76], and a needle [16] flex unit. The needle hub [76] includes locking pads and 4 spring members, two spring members for each pad, that are used to hold the needle [16] and needle hub [76] in their initial position or are used to lock the needle [16] and needle hub [76] in their locked position for disposal.

Figure 4A:
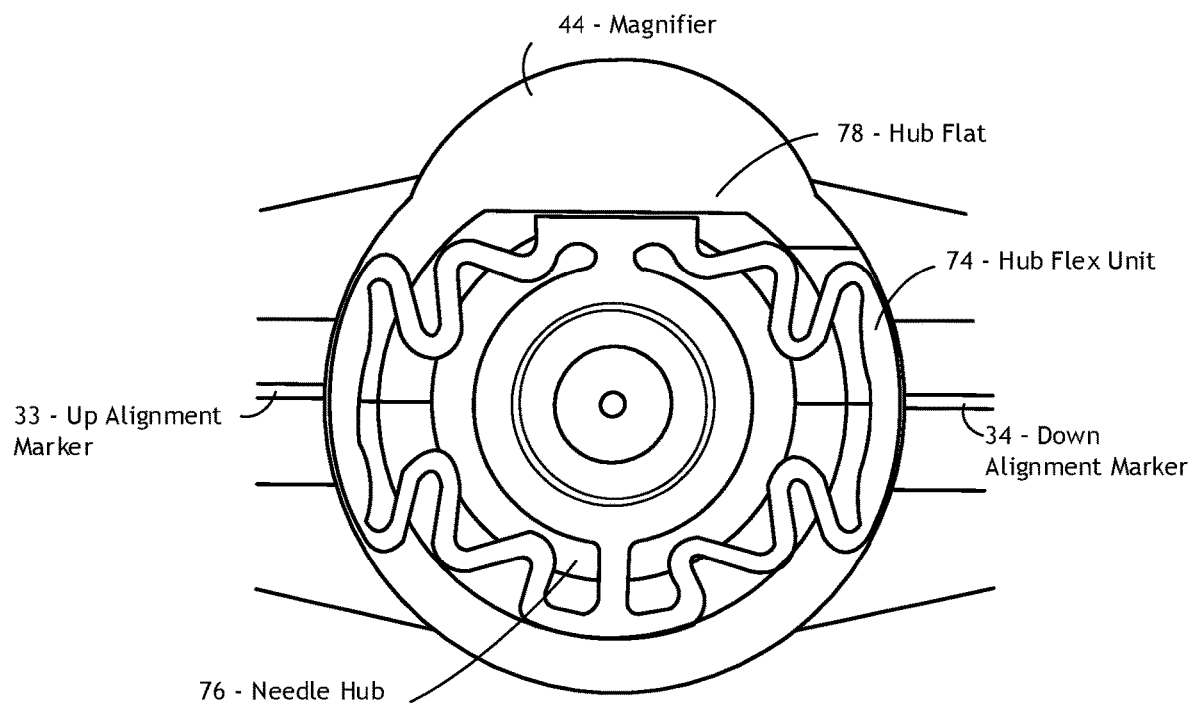
FIG. 4A depicts a cross sectional view through the safety cover and the needle and needle hub. This shows the red stripe, on the left, the needle bevel is up toward the red stripe and the green stripe is on the right. Also depicted is the needle hub indexing flat toward the magnifier. This design insures that the needle is always pointed upward toward the red stripe, is always 90 degrees from the needle hub flat and that the needle, the needle bevel, the needle hub are always indexed, with respect to the safety cover, enabling the needle bevel to be toward the red stripe, when viewed through the magnifier or gives the user knowledge of the position of the needle bevel position relative on the safety cover.

FIG. 4A depicts a cross sectional view through the safety cover [30] and the needle [16] and needle hub [76]. This shows the red stripe, on the left, the needle bevel [18] up toward the red stripe and the green stripe on the right. Also depicted is the needle hub [76] indexing flat [78] toward the magnifier. This design insures that the needle [16] is always pointed upward toward the red stripe, is always 90 degrees from the needle hub flat [78] and that the needle [16], the needle bevel [18], the needle hub [76] are always indexed, with respect to the safety cover [30], enabling the needle bevel [18] to be toward the red stripe, when viewed through the magnifier or gives the user knowledge of the position of the needle bevel position relative on the safety cover [30]. This shows the red stripe, on the left, the needle bevel [18] up toward the red stripe and the green stripe on the right. It also shows the needle hub indexing flat [78] toward the magnifier. This design ensures that the needle [16] is always pointed up toward the red stripe, is always 90 degrees from the needle hub flat [78] and that the needle [16], the needle bevel [18], the needle hub [76] are always indexed, with respect to the safety cover [30], enabling for the needle bevel [18] to be toward the red stripe, when viewed through the magnifier or provides the medical professional knowledge of the position of the needle bevel [18] relative to the red stripe on the safety cover [30].

Figure 4B:
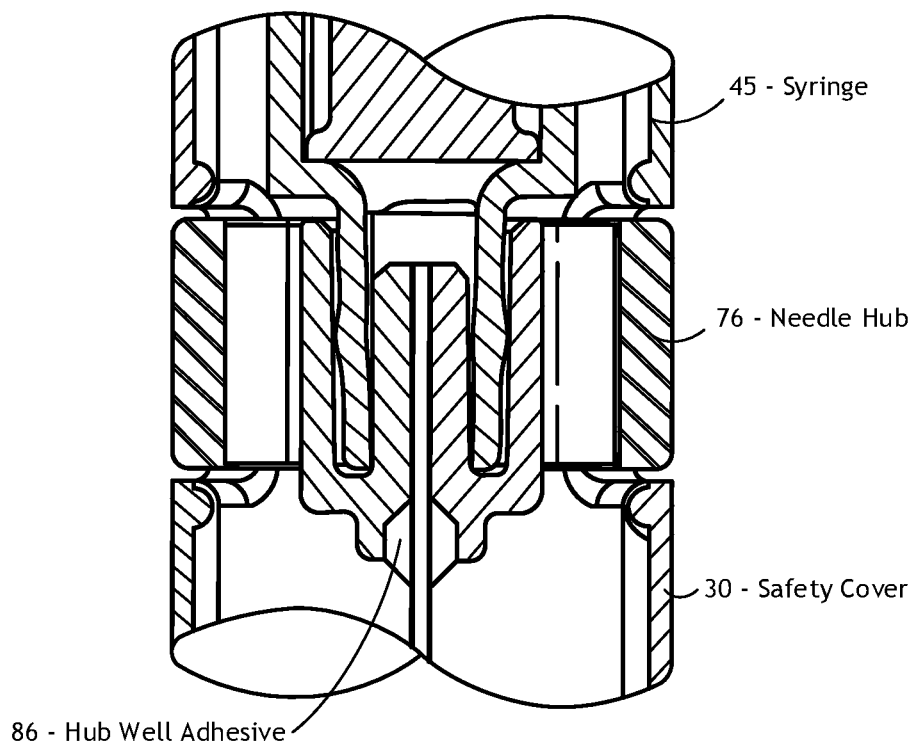
FIG. 4B depicts a cross sectional view through the safety cover, the needle, the needle hub and the syringe of the safety syringe assembly of FIG. 4A. The end of the syringe attaches to the needle hub, with the raised bump ring on the end of the syringe. This shows how the safety syringe assembly of the present invention are compatible with existing syringe designs.

FIG. 4B depicts a cross sectional view through the safety cover [30], the needle [16], the needle hub [76] and the syringe [45] of the safety syringe assembly [10] of FIG. 4A. The end of the syringe [45] attaches to the needle hub [76], with the raised bump ring on the end of the syringe [45]. This shows how the safety syringe assembly of the present invention [10] are compatible with existing syringe designs. FIG. 4B shows how the end of the syringe [45] attaches to the needle hub assembly [70], with the raised bump ring on the end of the syringe [45]. This design enables the safety syringe assembly [10] of the present invention to be compatible with an existing syringe design. This syringe design is made in the millions each year. Slight modifications to the needle hub [76] can be made enabling the safety syringe assembly [10] to be used with other standard medical syringes.

Figure 5:
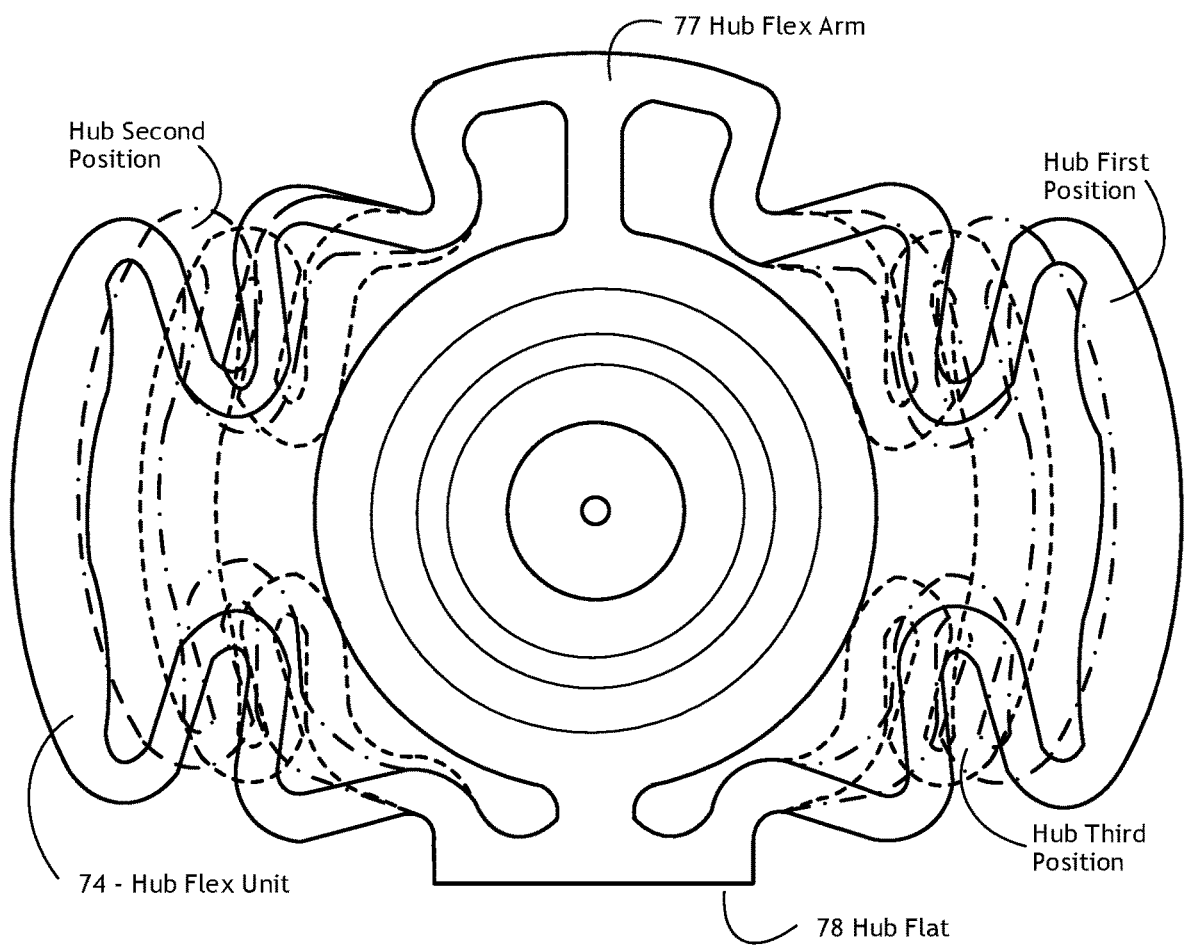
FIG. 5 depicts the hub assembly of the safety syringe assemble of FIGS. 1A, 1B, and 1C, highlighting the hub flex unit, the hub flex unit being in a first position during shipping, the hub flex unit being in a second position during insertion of the needle into the skin of the patient, and the hub flex unit being in a third position after the needle has been inserted into the skin of the patient awaiting disposal.

FIG. 5 depicts the hub assembly of the safety syringe assemble of FIGS. 1A, 1B, and 1C, highlighting the hub flex unit, the hub flex unit being in a first position during shipping, the hub flex unit being in a second position during insertion of the needle [16] into the skin of the patient, and the hub flex unit being in a third position after the needle [16] has been inserted into the skin of the patient awaiting disposal.

The safety syringe assembly of the present invention [10] enables the medical technician or user to push one or two buttons on the needle hub [76], releasing the needle [16] and hub from an initial safety position. After the release, the syringe [45], protected needle [16] and safety cover [30] can be placed on the top of the vial of allergy fluid and be safely inserted into the vial for the extraction of the fluid into the syringe [45]. This protects the medical technician or user from the potential stick hazard of an exposed needle [16] during the process of extracting fluid from the vial.

Figure 6:
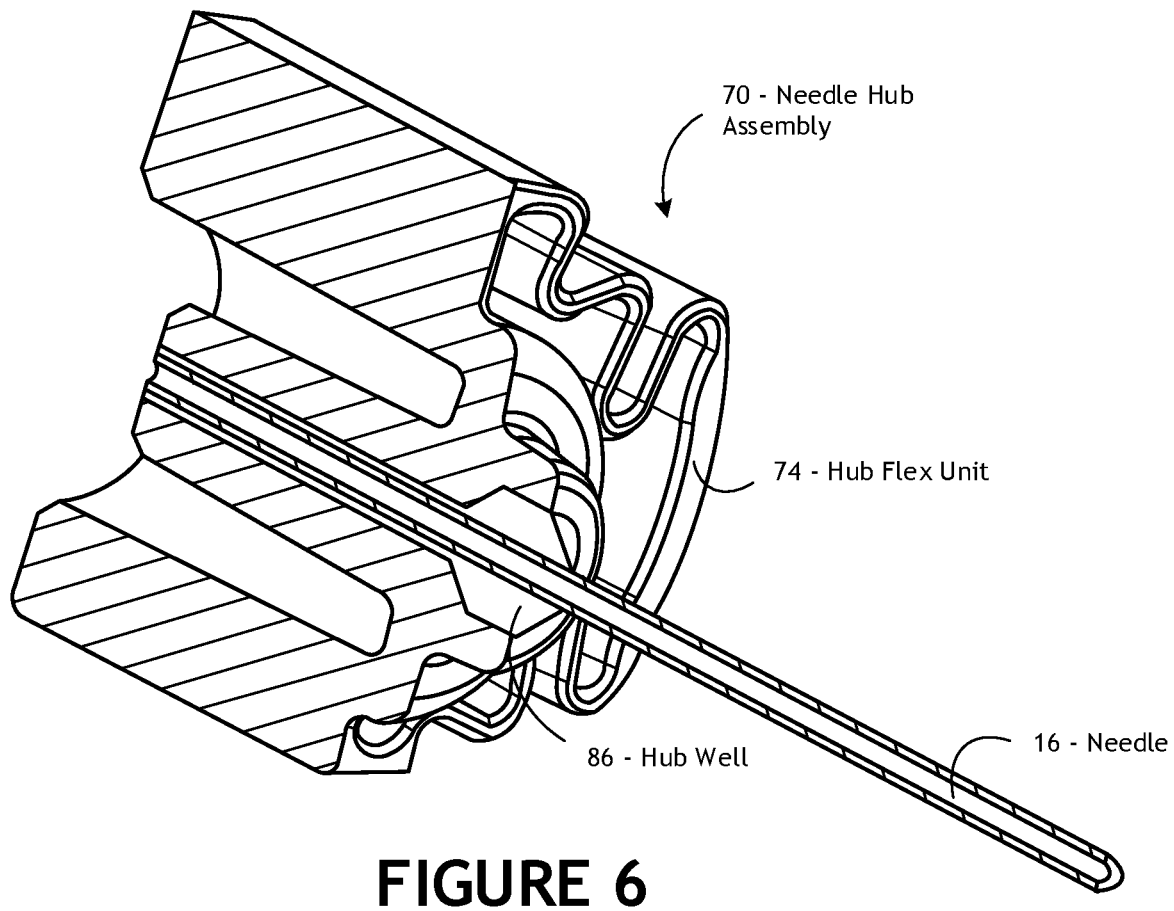
FIG. 6 depicts a half-section of the needle hub assembly of FIG. 3A.

FIG. 6 depicts a half-section of the needle hub assembly [70] of FIG. 3A. The hub well, into which the cannula is inserted, has two functions. The hub well [86] helps to align the adhesive-dispensing tip with the cannula-to-hub bond joint and the hub well [86] helps to promote adhesive flow into the bond line.

Figure 7:
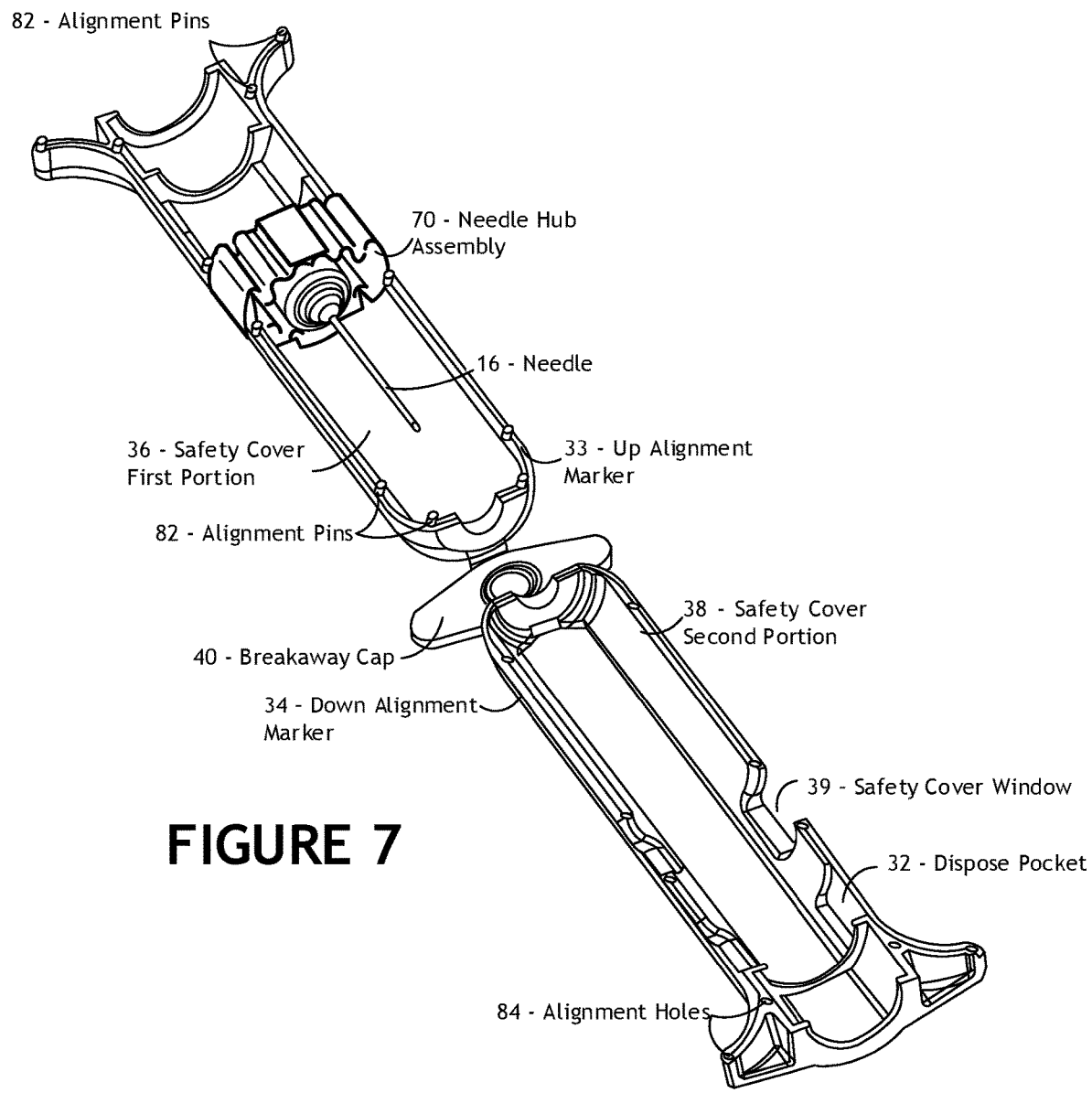
FIG. 7 depicts the needle hub assembly of FIGS. 3A and 3B positioned in one half of the safety cover for use in the safety syringe assembly of FIG. 2, the safety cover including two halves joined together by the safety cover.

FIG. 7 depicts the needle hub assembly of FIGS. 3A and 3B positioned in one half of the safety cover [30] for use in the safety syringe assembly [10] of FIG. 2, the safety cover [30] including two halves joined together by the breakaway cap [40].

The needle [16] and needle hub [76] are inserted into a half [36] of the safety cover without the magnifier. It also shows the needle [16] and needle hub [76] in their initial position. After the needle [16] and needle hub [76] are placed into this position, an adhesive can be placed on the edge of half of the safety cover [30] and the safety cover [30] is closed, creating the safety cover [30], needle [16] and needle hub assembly [70]. This safety syringe assembly [10] is now ready to have the syringe [45] inserted.

Figure 8:
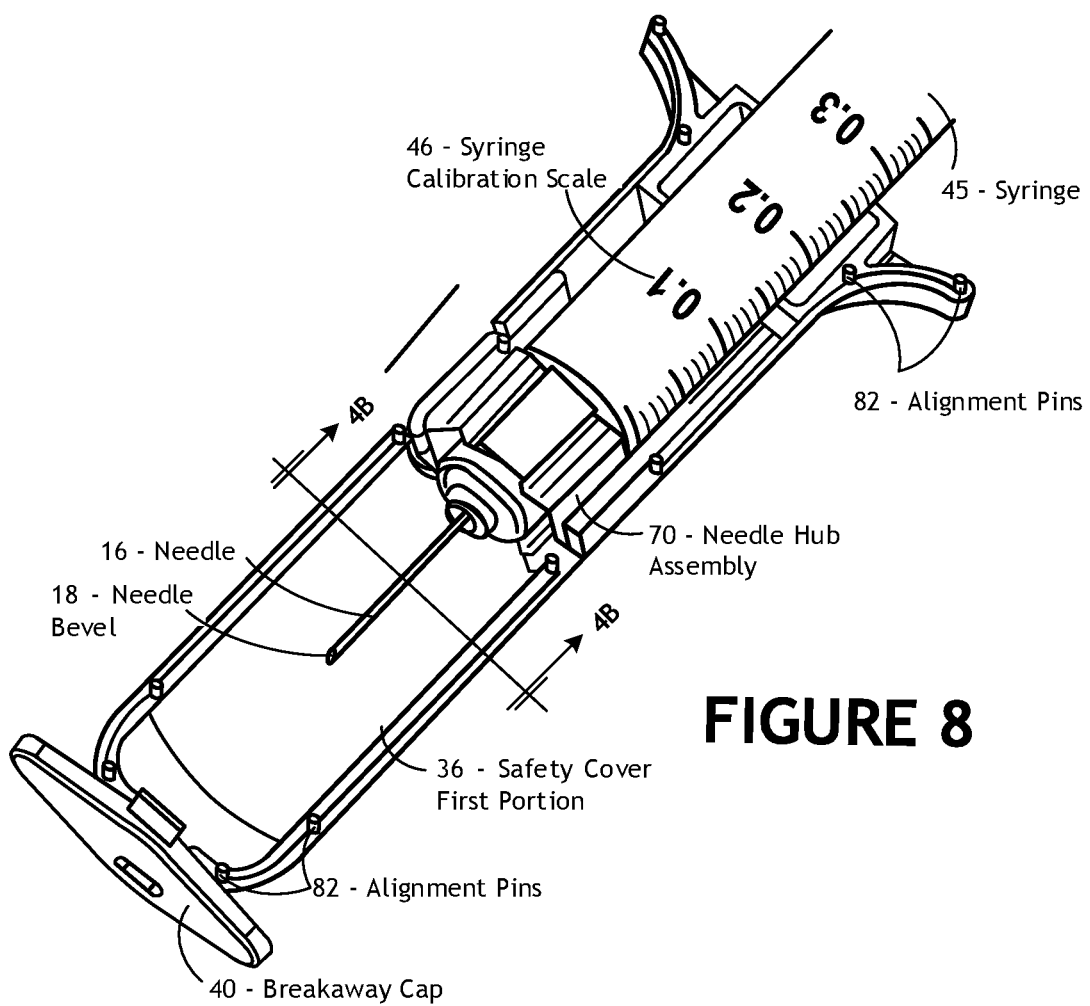
FIG. 8 depicts the needle and needle hub placed into half of the safety cover of FIG. 2, the needle and needle hub, in the first position with the syringe attached to the needle hub.

FIG. 8 depicts the needle [16] and needle hub [76] placed into half of the safety cover [30] of FIG. 2, the needle [16] and needle hub [76], in the first position with the syringe [45] attached to the needle hub [76].

The needle [16] and needle hub [76] are shown into half of the safety cover, the needle [16] and needle hub [76], in their initial position, with the syringe [45] attached to the needle hub [76]. The syringe volume scale [46] does not have to be placed in this position because it can be rotated, later, on the needle hub [76], to enable the scale [46] to be visible through the magnifier.

To initiate operation, the syringe [45] is pushed firmly into the needle hub [76] taking care not to depress the flex arms [77].

Figure 9:
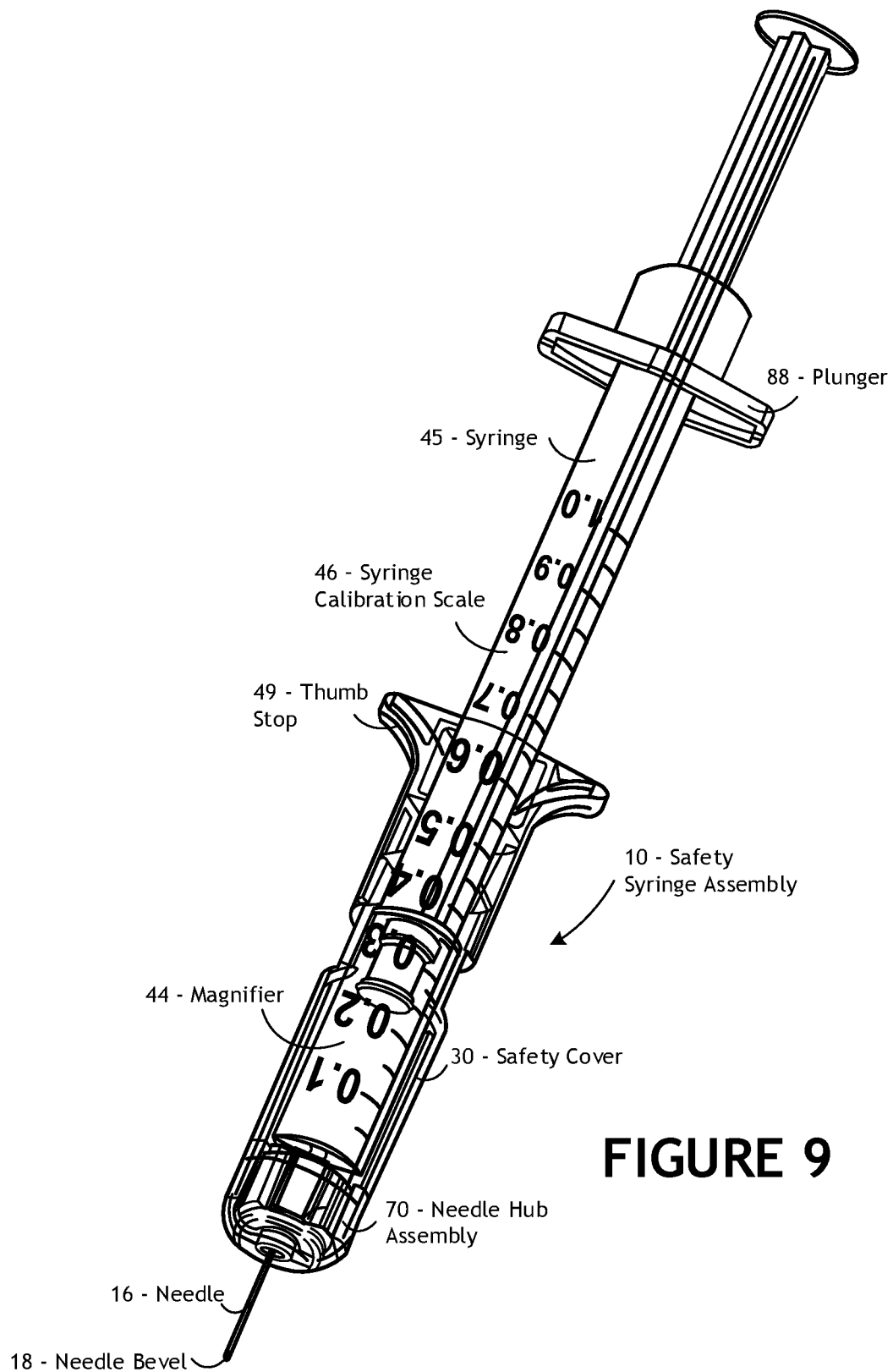
FIG. 9 depicts the safety cover assembly of FIGS. 1A, 1B, and 1C and a syringe in position that enables for filling of the device from the vial of medical fluid. The safety cover magnifies the volume scale to ensure that the proper amount of fluid is drawn.

FIG. 9 depicts the safety cover [30] assembly of FIGS. 1A, 1B, and 1C and a syringe [45] in position that enables for filling of the device from the vial of medical fluid. The safety cover [30] magnifies the volume scale [46] to ensure that the proper amount of fluid is drawn.

The safety cover [30] includes magnification to magnify the volume scale [46] on the syringe [45], for both a long and short needle, and magnifies a large portion of the volume scale [46]. Magnifying is particularly important when injecting low doses (0.01 to 0.30 ml) and permitting the practitioner, nurse, or user to detect air bubbles that can significantly alter the amount of allergen drawn into the syringe [45] and can also increase the risk of blood clots developing in the patient after injection. In addition, magnification can significantly affect the reproducibility of the skin test wheal (bleb) when comparing the saline negative control injection to the actual allergy injection. Proper intradermal allergy testing requires inserting the needle [16] under skin bevel [18] up and rotating the needle [16] 180 degrees and injecting the allergen bevel [18] down to prevent splashback on the practitioner, nurse, or user if the needle bevel [18] is not fully inserted and to have all of the allergy tests injected needle bevel [18] down so every test is done the same way by all practitioners.

For scale alignment, when the thumb stop [49] and the plunger [88] are aligned, the scale [46] appears in the magnifying window and the needle bevel [18] faces upward.

The safety cover magnifier magnifies the volume scale [46] to ensure that the proper amount of fluid is drawn into the syringe [45]. With the needles and syringes, used today, it is difficult to read the small graduations, on the syringe volume scale [46]. Without drawing in the proper amount of allergy fluid, false positives or false negatives are possible, during testing. Without the proper volume of allergy fluid being drawn into the syringe [45], allergy injections could be less affective.

FIG. 10 depicts another preferred embodiment of the safety cover [30] for use with the safety syringe assembly [110] of the present invention with a lock lever [112] to enable unobstructed movement of the needle hub assembly [170] from the second position to the third position along with a Detail "A" of the lock lever [112]. The lock lever ensures that the flex arm [77] of the needle hub assembly [70] will not become reengaged with the window [39] of the safety cover [30].

FIG. 11 depicts yet another preferred embodiment of the safety cover [30] for use with the safety syringe assembly [10] of the present invention with a lock lever [212] to enable unobstructed movement of the needle hub assembly [70] from the second position to the third position along with a Detail "B" of the lock lever [212]. The lock lever ensures that the flex arm [77] of the needle hub assembly [70] will not become reengaged with the window [39] of the safety cover [30].

Figure 12A:
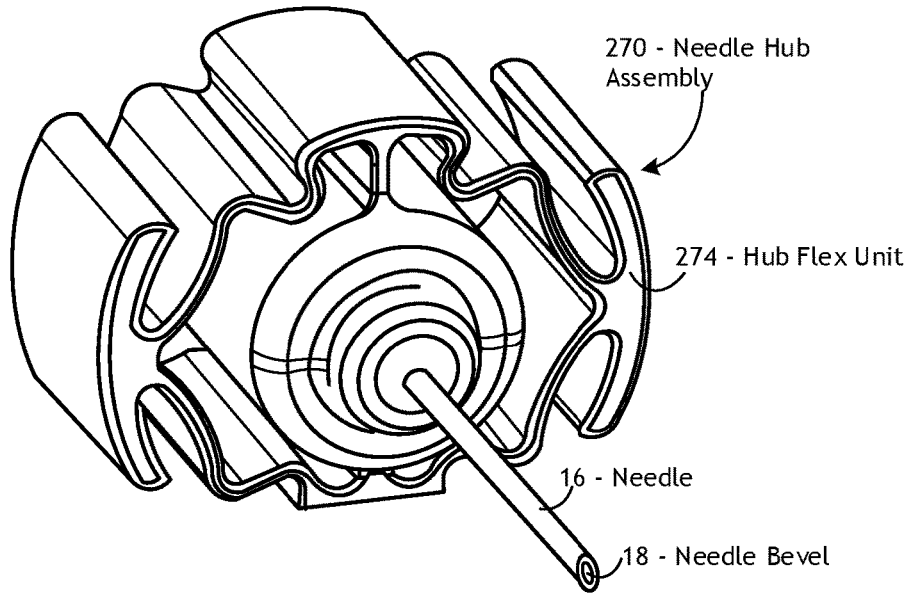
FIG. 12A depicts a front view and FIG. 12B depicts a rear view of a second preferred embodiment of the needle hub assembly of FIGS. 1A, 1B, and 1C, including the needle, a needle hub, and a needle flex unit.
Figure 12B:
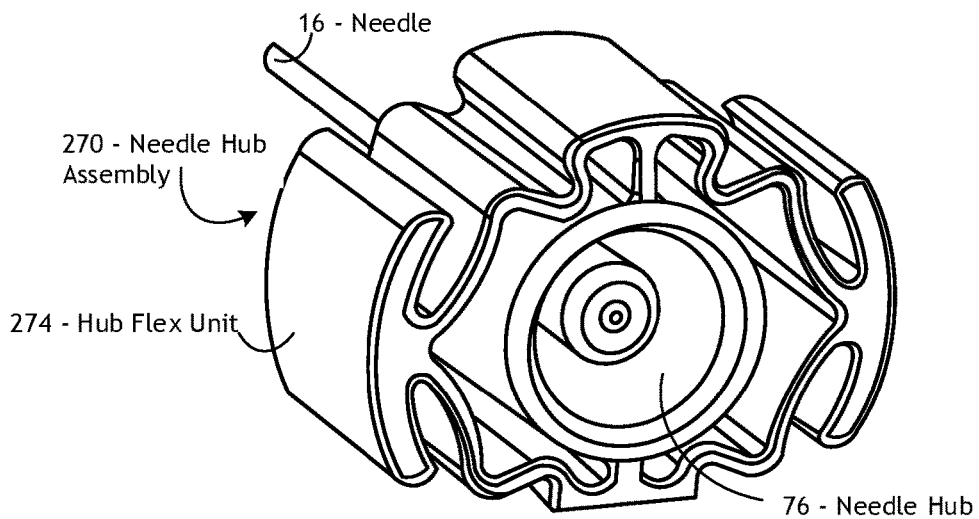

FIG. 12A depicts a front view and FIG. 12B depicts a rear view of a second preferred embodiment of the needle hub assembly [70] of FIGS. 1A, 1B, and 1C, including the needle [16], a needle hub [76], and a needle flex unit. The needle hub assembly [70] includes locking pads and four spring members, two spring members for each pad, that are used to hold the needle [16] and needle hub [76] in their initial position or are used to lock the needle [16] and needle hub [76] in their locked position for disposal.

To perform a visual check, the needle [16] should be clearly visible in the magnifier [44] of the safety cover with the needle bevel [18] facing toward the red stripe.

To initiate filling, the one or more flex arms [77] are pressed, and the safety cover [30] slides back on the syringe [45] to expose the needle [16]. Then fill the safety syringe assembly of the present invention [10] to the desired level, as the cap is unlocked into this position, as the syringe [45] is held and the plunger [88] is pulled to fill.

To dispose after dispensing, pull the plunger [88] back so that the needle hub assembly [70] is in the shipping position and depress the arms [77] again, continuing pulling until the needle hub assembly [70] snaps into the dispose pockets [32] and the syringe [45] pops off.

The release points on the needle hub [76] are tapered such that after injection, the safety cover [30] can be moved into a locked position that insures that the needle [16] with allergy fluid, potential blood and bodily fluid will not expose the medical technician or user to any bio-hazards because the safety cover [30] will completely cover the needle [16].

The safety cover [30], with the needle [16] and needle hub [76] in the locked position lock the safety cover [30], needle [16] and needle hub [76] together such that this bio-hazard can be properly disposed of, in a sharps container and the syringe [45] can be separated from the safety cover [30], needle [16] and needle hub [76] for recycling by placing the syringe [45] in a separate container.

For shipping, the hub with flex arms [77] are positioned in shipping windows with the needle [16] pointing toward sharps guard and needle bevel [18] toward red stripe.

The syringe [45] can be rotated to any position, but the needle bevel [18] will maintain its position.

The safety syringe assembly [10] is snapped off and disposed of in recycling. The needle hub assembly [70] is locked into the dispose pocket [32] and cannot be dislodged easily. The needle [16] is contained and is disposed of in the sharps container while the syringe [45] is recycled.

Throughout this application, various Patents and Applications are referenced by number and inventor. The disclosures of these documents in their entireties are hereby incorporated by reference into this specification in order to more fully describe the state of the art to which this invention pertains.

It is evident that many alternatives, modifications, and variations of the safety syringe assembly of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10—Safety Syringe Assembly-1st Embodiment
16—Needle
18—Needle Bevel
30—Safety Cover
32—Dispose Pocket
33 and 34—Up and Down Alignment Markers
36 and 38—Safety Cover First and Second Portions
39—Safety Cover Window
40—Breakaway Cap
44—Magnifier
45—Syringe
46—Syringe Calibration Scale
49—Thumb Stop
70—Needle Hub Assembly
74—Hub Flex Unit
76—Needle Hub
77 and 78—Hub Flex Arm and Hub Flat
82—Alignment Pins
84—Alignment Holes
86—Hub Well
88—Plunger
110—Safety Syringe Assembly-2$^{nd}$ Embodiment
112—Lock Lever
170—Needle Hub Assembly
212—Lock Lever

The invention claimed is:

1. A safety syringe assembly comprising:
   a) a needle having a bevel;
   b) a needle hub assembly including said needle disposed in a hub flex unit, said hub flex unit being mounted upon a needle hub, said needle hub retaining said needle mounted in a secure manner, said hub flex unit including a flex arm; and
   c) a safety cover, said needle and said needle hub assembly being disposed within said safety cover, said safety cover including a window, said flex arm cooperatively engaging with said window to prevent said needle hub assembly from sliding within said safety cover during shipping, filling of said safety syringe assembly with medical fluid being initiated by pressing said flex arm into said window of said safety cover;
      i. said needle hub assembly being securely positionable within said safety cover in a shipping position, said shipping position of hub flex unit having a first diameter;
      ii. said needle hub assembly being securely positionable within said safety cover in an insertion position, said insertion position being for needle insertion, said insertion position being different from said shipping position, said insertion position of said hub flex unit having a second diameter; and
      iii. said needle hub assembly being securely positionable within said safety cover in a disposal position for disposal after said needle has been used, said disposal position being different from said insertion position and said shipping position, said disposal position of said hub flex unit having a third diameter.

2. The safety syringe assembly of claim 1, further comprising said safety cover having a first and second portion, a breakaway cap being positioned between said first and second portion.

3. The safety syringe assembly of claim 1, wherein a portion of said safety cover is made of a clear material enabling light to pass therethrough, said portion including magnification enabling a user to view a dosage calibration scale, said needle bevel, and air bubbles.

4. The safety syringe assembly of claim 3, further comprising said safety cover including a thumb stop and said safety syringe assembly including a plunger, wherein when said thumb stop and said plunger are in alignment, said dosage calibration scale is within said magnification and said needle bevel is visible.

5. The safety syringe assembly of claim 1, wherein said shipping position of said safety cover is disposed between said insertion position and said disposal position, said safety cover further comprises a lock lever, said lock lever preventing said flex arm of said needle hub assembly from becoming reengaged with said window of said safety cover.

6. The safety syringe assembly of claim 1, wherein said needle and said needle hub are locked relative to said safety cover enabling said needle and said needle hub and said safety cover to be disposed in a first container and said syringe to be disposed separately in a second container.

7. The safety syringe assembly of claim 1, further comprising said hub flex unit including a flat, said flat cooperatively engaging with said window to prevent said needle hub assembly from rotating within said safety cover during shipping.

8. A safety cover for use with a safety syringe assembly, said safety cover including:
   a) a window; and
   b) a first portion and a second portion, a breakaway cap being positioned between said first portion and said second portion;
   said safety cover being securely engageable with a needle hub assembly positionable within said safety syringe assembly during shipping of said safety syringe assembly, said window of said safety cover assembly being cooperatively engageable with a flex arm of said needle hub assembly, filling of said safety syringe assembly with medical fluid beginning by pressing said flex arm into said window;
      i. said safety cover being securely engageable with said needle hub assembly within said safety cover in a shipping position during said shipping of said safety syringe assembly;
      ii said safety cover being securely engageable with said needle hub assembly within said safety cover in an insertion position of said safety syringe assembly, said insertion position being different from said shipping position; and iii. said safety cover being securely engageable with said needle hub assembly within said safety cover in a disposal position after said safety syringe assembly has been used, said disposal position being different from said insertion position and said shipping position.

9. The safety cover of claim 8, wherein said shipping position of said safety cover is disposed between said insertion position and said disposal position, said safety cover further comprising a lock lever, said lock lever preventing said first member of said needle hub assembly from becoming reengaged with said window of said safety cover.

10. The safety cover of claim 8, wherein a portion of said safety cover is made of a clear material enabling light to pass therethrough, said portion including magnification, enabling a user to view a dosage calibration scale and air bubbles.

11. The safety cover of claim 8, wherein a portion of said safety cover is made of a clear material enabling light to pass therethrough and includes magnification enabling a user to view a dosage calibration scale and air bubbles.

12. A safety syringe assembly comprising:
   a) a needle having a bevel;
   b) a needle hub assembly including said needle disposed in a hub unit, said needle being securely disposed within said needle hub assembly, said hub unit being mounted upon a needle hub, said needle hub retaining said needle securely mounted therewithin, said hub unit including a flex arm; and
   c) a safety cover, said needle and said needle hub assembly being disposed within said safety cover, said safety cover including a window, said flex arm preventing said needle hub assembly from sliding within said safety cover during shipping,
      i. said needle hub assembly being securely engageable within said safety cover in a shipping position during said shipping of said safety syringe assembly;
      ii. said needle hub assembly being securely engageable within said safety cover in an insertion position of said safety syringe assembly, said safety position being different from said shipping position; and
      iii. said needle hub assembly being securely engageable within said safety cover in a disposal position after said safety syringe assembly has been used, said shipping position being different from said insertion position and said disposal position, said shipping position being disposed between said insertion position and said disposal position; filling of said safety syringe assembly with medical fluid being initiated by pressing said flex arm into said window of said safety cover.

13. The safety syringe assembly of claim 12, wherein said hub unit varies in diameter in said shipping position, in said insertion position, and in said disposal position of said safety cover.

14. The safety syringe assembly of claim 12, wherein said needle and said needle hub are locked relative to said safety cover enabling said needle and said needle hub and said safety cover to be disposed in a first container and said syringe to be disposed separately in a second container.

15. The safety syringe assembly of claim 12, wherein a portion of said safety cover is made of a clear material enabling light to pass therethrough, said portion including magnification, enabling a user to view a dosage calibration scale, said needle bevel and air bubbles.

16. The safety syringe assembly of claim 15, further comprising said needle hub assembly including a thumb stop and a plunger, wherein when said thumb stop and said plunger are in alignment, said dosage calibration scale is within said magnification and said needle bevel is visible.

17. The safety syringe assembly of claim 12, further comprising a lock lever that prevents said flex arm of said needle hub assembly from becoming reengaged with said window of said safety cover.

18. The safety syringe assembly of claim 12, further comprising said safety cover having a first and a second portion, a breakaway cap being positioned between said first portion and said second portion.

19. The safety syringe assembly of claim 12, wherein depressing said window of said safety cover initiates movement of said needle hub assembly from said shipping position into said insertion position.

20. The safety syringe assembly of claim 12, further comprising said hub unit including a flat, said flat cooperatively engaging with said window to prevent said needle hub assembly from rotating within said safety cover during shipping.

* * * * *